(12) United States Patent
Dai (10) Patent No.: US 7,342,109 B2
(45) Date of Patent: Mar. 11, 2008

(54) HUMAN KINASE INTERACTING PROTEIN 2 (KIP2)-RELATED GENE VARIANT ASSOCIATED WITH CANCERS

(76) Inventor: Ken-Shwo Dai, 1F., No. 9, Industry E. Rd., JV, Science-Based Industrial Park, Hsinchu (TW)

( * ) Notice: Subject to any disclaimer, the term of this patent is extended or adjusted under 35 U.S.C. 154(b) by 387 days.

(21) Appl. No.: 11/125,403

(22) Filed: May 9, 2005

(65) Prior Publication Data

US 2006/0040285 A1    Feb. 23, 2006

Related U.S. Application Data

(63) Continuation-in-part of application No. 10/103,334, filed on Mar. 21, 2002, now abandoned.

(51) Int. Cl.
| | |
|---|---|
| *C07H 21/00* | (2006.01) |
| *C07H 5/00* | (2006.01) |
| *C08B 37/00* | (2006.01) |
| *A61K 38/00* | (2006.01) |
| *C07K 14/00* | (2006.01) |
| *C07K 16/00* | (2006.01) |
| *C07K 17/00* | (2006.01) |
| *C07K 1/00* | (2006.01) |
| *A61K 35/14* | (2006.01) |
| *C12P 21/06* | (2006.01) |
| *C12P 19/34* | (2006.01) |
| *C12Q 1/00* | (2006.01) |
| *C12Q 1/68* | (2006.01) |
| *G01N 33/48* | (2006.01) |

(52) U.S. Cl. ............... 536/23.5; 536/18.7; 536/23.1; 530/300; 435/69.1

(58) Field of Classification Search .......... 536/18.7, 536/23.1, 23.5; 530/300; 435/69.1
See application file for complete search history.

(56) References Cited

U.S. PATENT DOCUMENTS

| 6,190,857 B1 | 2/2001 | Ralph et al. | |
|---|---|---|---|
| 2007/0083334 A1* | 4/2007 | Mintz et al. | ........... 702/19 |

OTHER PUBLICATIONS

Yerushalmi, et al. (*Gene*, 2001, vol. 265, pp. 55-60).
Caillou, et al. (*Journal of Clinical Endocrinology and Metabolism*, 2001, vol. 86, pp. 3351-3358).
Conklin, et al. (*Briefings in Bioinformatics*, 2000, vol. 1, pp. 93-99).
Seki, et al., *Biochim. Biophys. Acta*, 1999, vol. 1444, pp. 143-147.
Sethi, T. "Science, Medicine, and the Future: Lung Cancer" *BMJ*, 314 (7081) : 652 (1997).
Kondo, M., et al. "Selective Maternal-Allele Loss in Human Lung Cancers of the Maternally Expressed p57K KIP2 Gene at 11p15.5" *Oncogene*, vol. 12, p. 1365-1368 (1996).
Bepler, G., et al. "Three Tumor-Suppressor Regions on Chromosome 11p Identified by High-Resolution Deletion Mapping in Human . . . Cancer" *Proc. Natl. Acad. Sci. USA*, vol. 91, pp. 5513-5517 (1994).
Chung, W-Y., et al. "Chromosome 11p15.5 Regional Imprinting: Comparative Analysis of KIP2 and H19 in Human . . . Wilms' Tumors" *Human Molecular Genetics*, vol. 5, No. 8, pp. 1101-1108 (1996).
Matsuoka, S., et al. "p57KIP2, a Structurally Distinct Member of the p21CIP1 Cdk Inhibitor Family, is a Candidate Tumor Suppressor Gene" *Genes & Development*, vol. 9, pp. 650-662 (1995).
"On the Preparation and Utilization of Isolated and Purified Oligonucleotides" [electronic resource], Andrew Chin, allegedly deposited in UNC library on Mar. 14, 2002, date of publication, if any, is in question.

* cited by examiner

*Primary Examiner*—Alana M. Harris
(74) *Attorney, Agent, or Firm*—Ladas and Parry LLP (57) ABSTRACT

Nucleic acid and polypeptide sequences of one novel human KIP2-related gene variant (KIP2V), and the processes for producing the same are provided. Use of the nucleic acid and polypeptide sequences of the gene variant in diagnosing cancers is also provided.

4 Claims, 7 Drawing Sheets

Fig. 1

```
GGCGGCCACCATGGGGAACAAGCAGACCATCTTCACCGAAGAGCAGCTAGACAACTACCA  60
              M  G  N  K  Q  T  I  F  T  E  E  Q  L  D  N  Y  Q  17
GGACTGCACCTTCTTCAATAAGAAGGACATCCTCAAGAGAATCCCTTCAAAGAAAGGATC 120
   D  C  T  F  F  N  K  K  D  I  L  K  R  I  P  S  K  K  G  S 37
GTGGCGGCGTTTTCCGAGGATGGTGAGGGGAACCTCACTTTCAACGACTTTGTGGACATG 180
   W  R  R  F  P  R  M  V  R  G  T  S  L  S  T  T  L  W  T  C 57
TTTTCCGTGCTCTGCGAGTCGGCTCCCCGAGAGCTCAAGGCAAACTATGCCTTCAAGATC 240
   F  P  C  S  A  S  R  L  P  E  S  S  R  Q  T  M  P  S  R  S 77
TATGACTTCAACACTGACAACTTCATCTGCAAGGAGGACCTGGAGCTGACGCTGGCCCGG 300
   M  T  S  L  T  T  S  S  A  R  R  T  W  *                   92
CTCACTAAGTCAGAGCTGGATGAGGAGGAGGTGGTGCTTGTGTGCGACAAGGTCATTGAG 360
GAGGCTGACTTGGATGGTGACGGCAAGCTGGGCTTTGCTGACTTCGAGGACATGATTGCC 420
AAGGCCCCTGACTTCCTCAGCACTTTCCACATCCGGATCTGAGGACACTGCCGAGGCTGT 480
AGGGGCCTAGAAGTCCACCATCCTGCCCTGCAGTCACATGGGTGTGGCCTCCAAGCTCCC 540
CAGGAAAGCAGTGGCAGCCTCTGGGGTTTACACCACAAATATATCCTGTGGCCCTTTCAG 600
CAAAAAAAAAACCTTAACCAGGAAGGGGGCCTGTGAAGGTTAGGACCCTTCCCACAGCCC 660
CGCTGTGGTCCAGCCCCGGGACCCATGGCCTCTCTCCAGGCCCTCCGCACCCCGCCCCAT 720
GCCCCAGTCCTTTCCTACTCCAGAAATGCTCCCCACCCCCCCAAGAGGGAAAAGCAGATA 780
ACCCAACAGGAGGTGGTGGGGTCTGACGTGTCCAAGTGCTGGCAGACACCCTGGTCACCC 840
AGGACAGAGCGGAAAAAAAAAAAGAGGTCAGGGTTTTAACGAGCTATGCAATCTTTTTC  900
CAAAACCCAAGGTTGGGCTGCTTCCCACCCCTGCCTGTTCCCCTTCTCCCGGCCTCCTTC 960
ACAATGTGAAGCTGTGGGTGCAGTGGCGCCAAGGGCTCTTGCTCCTGTCTCTGCCTCTGG 1020
GTCATGAGTACCACCCTGCCTGCCTCCCCAACACCGTGGAATCCTCACTGGTGTGCTGTC 1080
CACAGATTTGTGAACTCCTGGTAGTAAAACACTTTTGCATCCA                  1123
```

Fig. 2A

```
       1                                                            60
KIP2V  GGCGGCCACCATGGGGAACAAGCAGACCATCTTCACCGAAGAGCAGCTAGACAACTACCA
KIP2   ----GCCACCATGGGGAACAAGCAGACCATCTTCACCGAAGAGCAGCTAGACAACTACCA 61                                                           120
KIP2V  GGACTGCACCTTCTTCAATAAGAAGGACATCCTCAAG-----------------------
KIP2   GGACTGCACCTTCTTCAATAAGAAGGACATCCTCAAGCTGCATTCGCGATTCTATGAGCT 121                                                          180
KIP2V  ------------------------------------------------------------
KIP2   GGCCCCCAACCTCGTCCCAATGGACTACAGGAAGAGCCCCATCGTCCACGTGCCCATGAG 181                                                          240
KIP2V  --------------------------AGAATCCCTTCAAAGAAAGGATCGTGGCGGC
KIP2   CCTCATCATCCAGATGCCAGAGCTCCGGGAGAATCCCTTCAAAGAAAGGATCGTGGCGGC 241                                                          300
KIP2V  GTTTTCCGAGGATGGTGAGGGGAACCTCACTTTCAACGACTTTGTGGACATGTTTTCCGT
KIP2   GTTTTCCGAGGATGGTGAGGGGAACCTCACTTTCAACGACTTTGTGGACATGTTTTCCGT 301                                                          360
KIP2V  GCTCTGCGAGTCGGCTCCCCGAGAGCTCAAGGCAAACTATGCCTTCAAGATCTATGACTT
KIP2   GCTCTGCGAGTCGGCTCCCCGAGAGCTCAAGGCAAACTATGCCTTCAAGATCTATGACTT 361                                                          420
KIP2V  CAACACTGACAACTTCATCTGCAAGGAGGACCTGGAGCTGACGCTGGCCCGGCTCACTAA
KIP2   CAACACTGACAACTTCATCTGCAAGGAGGACCTGGAGCTGACGCTGGCCCGGCTCACTAA 421                                                          480
KIP2V  GTCAGAGCTGGATGAGGAGGAGGTGGTGCTTGTGTGCGACAAGGTCATTGAGGAGGCTGA
KIP2   GTCAGAGCTGGATGAGGAGGAGGTGGTGCTTGTGTGCGACAAGGTCATTGAGGAGGCTGA
```

Fig. 2B

```
      481                                                    540
KIP2V CTTGGATGGTGACGGCAAGCTGGGCTTTGCTGACTTCGAGGACATGATTGCCAAGGCCCC
KIP2  CTTGGATGGTGACGGCAAGCTGGGCTTTGCTGACTTCGAGGACATGATTGCCAAGGCCCC 541                                                    600
KIP2V TGACTTCCTCAGCACTTTCCACATCCGGATCTGAGGACACTGCCGAGGCTGTAGGGGCCT
KIP2  TGACTTCCTCAGCACTTTCCACATCCGGATCTGAGGACACTGCCGAGGCTGTAGGGGCCT 601                                                    660
KIP2V AGAAGTCCACCATCCTGCCCTGCAGTCACATGGGTGTGGCCTCCAAGCTCCCCAGGAAAG
KIP2  AGAAGTCCACCATCCTGCCCTGCAGTCACATGGGTGTGGCCTCCAAGCTCCCCAGGAAAG 661                                                    720
KIP2V CAGTGGCAGCCTCTGGGGTTTACACCACAAATATATCCTGTGGCCCTTTCAGCAAAAAAA
KIP2  CAGTGGCAGCCTCTGGGGTTTACACCACAAATATATCCTGTGGCCCTTTCAGCAAAAAAA 721                                                    780
KIP2V AAACCTTAACCAGGAAGGGGGCCTGTGAAGGTTAGGACCCTTCCCACAGCCCCGCTGTGG
KIP2  AAACCTTAACCAGGAAGGGGGCCTGTGAAGGTTAGGACCCTTCCCACAGCCCCGCTGTGG 781                                                    840
KIP2V TCCAGCCCCGGGACCCATGGCCTCTCTCCAGGCCCTCCGCACCCCGCCCCATGCCCCAGT
KIP2  TCCAGCCCCGGGACCCATGGCCTCTCTCCAGGCCCTCCGCACCCCGCCCCATGCCCCAGT 841                                                    900
KIP2V CCTTTCCTACTCCAGAAATGCTCCCCACCCCCCCAAGAGGGAAAAGCAGATAACCCAACA
KIP2  CCTTTCCTACTCCAGAAATGCTCCCCACCCCCCCAAGAGGGAAAAGCAGATAACCCAACA 901                                                    960
KIP2V GGAGGTGGTGGGGTCTGACGTGTCCAAGTGCTGGCAGACACCCTGGTCACCCAGGACAGA
KIP2  GGAGGTGGTGGGGTCTGACGTGTCCAAGTGCTGGCAGACACCCTGGTCACCCAGGACAGA
```

Fig. 2C

```
        961                                                        1020
KIP2V   GCGGAAAAAAAAAAAAGAGGTCAGGGTTTTAACGAGCTATGCAATCTTTTTCCAAAACCC
KIP2    GCGGAAAAAAAAAAAAGAGGTCAGGGTTTTAACGAGCTATGCAATCTTTTTCCAAAACCC 1021                                                       1080
KIP2V   AAGGTTGGGCTGCTTCCCACCCCTGCCTGTTCCCCTTCTCCCGGCCTCCTTCACAATGTG
KIP2    AAGGTTGGGCTGCTTCCCACCCCTGCCTGTTCCCCTTCTCCCGGCCTCCTTCACAATGTG 1081                                                       1140
KIP2V   AAGCTGTGGGTGCAGTGGCGCCAAGGGCTCTTGCTCCTGTCTCTGCCTCTGGGTCATGAG
KIP2    AAGCTGTGGGTGCAGTGGCGCCAAGGGCTCTTGCTCCTGTCTCTGCCTCTGGGTCATGAG 1041                                                       1200
KIP2V   TACCACCCTGCCTGCCTCCCCAACACCGTGGAATCCTCACTGGTGTGCTGTCCACAGATT
KIP2    TACCACCCTGCCTGCCTCCCCAACACCGTGGAATCCTCACTGGTGTGCTGTCCACAGATT

1201
KIP2V   TGTGAACTCCTGGTAGTAAAACACTTTTGCATCCA    1123
KIP2    TGTGAACTCCTGGTAGTAAAACACTTTTGCATCCA    1231
```

Fig. 3

```
          1                                                           60
KIP2V  MGNKQTIFTEEQLDNYQDCTFFNKKDILK-------------------------------
KIP2   MGNKQTIFTEEQLDNYQDCTFFNKKDILKLHSRFYELAPNLVPMDYRKSPIVHVPMSLII 61                                                          120
KIP2V  ------------------------------------------------------------
KIP2   QMPELRENPFKERIVAAFSEDGEGNLTFNDFVDMFSVLCESAPRELKANYAFKIYDFNTD 121                                                         180
KIP2V  ------------------------------------------------------------
KIP2   NFICKEDLELTLARLTKSELDEEEVVLVCDKVIEEADLDGDGKLGFADFEDMIAKAPDFL 181                                                         240
KIP2V  -----RIPSKKGSWRRFPRMVRGTSLSTTLWTCFPCSASRLPESSRQTMPSRSMTSTLTT
KIP2   STFHIRI-----------------------------------------------------

241
KIP2V  SSARRTWS      92
KIP2   --------     187
```

HUMAN KINASE INTERACTING PROTEIN 2 (KIP2)-RELATED GENE VARIANT ASSOCIATED WITH CANCERS

This is a continuation-in-part of application Ser. No. 10/103,334 filed on Mar. 21, 2002 now abandoned claims the benefit thereof and incorporates the same by reference.

FIELD OF THE INVENTION

The invention relates to the nucleic acid and polypeptide sequences of a novel human kinase interacting protein 2 (KIP2)-related gene variant, preparation process thereof, and uses of the same in diagnosing cancers.

BACKGROUND OF THE INVENTION

Cancer is one of the major causes of deaths in the world. The number of new cancer cases is reported to be more than 10 million people every year and is estimated to be 15 million people by 2020. Cancer-related deaths are 6 million every year, representing 12% of deaths worldwide (National Cancer Control Programmes: Policies and Managerial Guidelines, World Health Organization Geneva, 2002). In the United States, the number of new cancer cases and deaths in 2005 is estimated to be 1,372,910 and 570,280 people, respectively (Cancer Facts & Figures-2005, American Cancer Society (ACS), Atlanta, Ga., 2005). In recent years, much progress has been made toward understanding the molecular and cellular biology of cancers. Many important contributions have been made by the identification of several key genetic factors associated with cancers. However, there are still some limitations in the use of biological markers for detecting cancers, suggesting that identification of new markers for diagnosing cancers is needed.

One of the contributing factors for cancers is the genes associated with cell cycle control. Thus, future strategies for the prevention and treatment of prostate cancer will be focused on identification, isolation and elucidation of genes involved in cell cycle regulation. A human kinase interacting protein 2 (KIP2) gene, candidate tumor suppressor gene (Matsuoka et al. (1995) Genes Dev 9:650-62), is a member of Cip/Kip family involved in the negative regulation of the cell cycle at the G1 checkpoint (Lee et al. (1995) Genes Dev 9:639-49; Harper and Elledge, (1996) Curr Opin Genet Dev 6:56-64; Sherr, (1996) Science 274:1672-7; Lee and Yang, (2001) Cell Mol Life Sci 58:1907-22). The tumor suppressor activity of KIP2 was shown to be mediated via its interaction with cyclin A-CDK2 (Adkins and Lumb, (2002) Proteins 46:1-7) or proliferating cell nuclear antigen (PCNA; Watanabe et al. (1998) Proc Natl Acad Sci USA 95:1392-1397). Overexpression of KIP2 was reported to arrest cells in G1 (Lee et al. (1995) Genes Dev 9:639-49; Matsuoka et al. (1995) Genes Dev 9:650-62). Decreased expression of KIP2 has been observed in many cancers (Chung et al. (1996) Hum Mol Genet 5:1101-8; Oya and Schulz, (2000) Br J Cancer 83:626-31; Dauphinot et al. (2001) Oncogene 20:3258-65; Ito et al. (2001) Oncology 61:221-5). These findings strongly implicate that KIP2 may have a role in the tumorigenic process of cancers. Therefore, the discovery of gene variants of KIP2 from cancers may be important targets for diagnostic markers of cancers.

SUMMARY OF THE INVENTION

The present invention provides one KIP2-related gene variant present in human cancers. The nucleotide sequence of the gene variant and polypeptide sequence encoded thereby can be used for the diagnosis of any diseases associated with this gene variant or cancers, in particular, the small cell lung cancer, lung adenocarcinoma, T-cell lymophoblastic lymphoma, glioblastoma, gastric carcinoma, colon adenocarcinoma, prostate carcinoma, pancreatic carcinoma, esophagus epidermoid carcinoma and promonocytic leukemia.

The invention further provides an expression vector and host cell for expressing the variant.

The invention further provides a method for producing the variant.

The invention further provides an antibody specifically binding to the variant.

The invention also provides methods for detecting the presence of the variant in a mammal.

DETAILED DESCRIPTION OF THE INVENTION

According to the present invention, all technical and scientific terms used have the same meanings as commonly understood by persons skilled in the art.

The term "antibody" used herein denotes intact molecules (a polypeptide or group of polypeptides) as well as fragments thereof, such as Fab, R(ab')$_2$, and Fv fragments, which are capable of binding the epitopic determinutesant. Antibodies are produced by specialized B cells after stimulation by an antigen. Structurally, antibody consists of four subunits including two heavy chains and two light chains. The internal surface shape and charge distribution of the antibody binding domain is complementary to the features of an antigen. Thus, antibody can specifically act against the antigen in an immune response.

The term "base pair (bp)" used herein denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool (BLAST; Altschul et al., (1997) Nucleic Acids Res. 25: 3389-3402)" used herein denotes programs for evaluation of homologies between a query sequence (amino or nucleic acid) and a test sequence as described by Altschul et al. (Nucleic Acids Res. 25: 3389-3402, 1997). Specific BLAST programs are described as follows:

(1) BLASTN compares a nucleotide query sequence against a nucleotide sequence database;

(2) BLASTP compares an amino acid query sequence against a protein sequence database;

(3) BLASTX compares the six-frame conceptual translation products of a query nucleotide sequence against a protein sequence database;

(4) TBLASTN compares a query protein sequence against a nucleotide sequence database translated in all six reading frames; and (5) TBLASTX compares the six-frame translations of a nucleotide query sequence against the six-frame translations of a nucleotide sequence database.

The term "cDNA" used herein denotes nucleic acids that synthesized from a mRNA template using reverse transcriptase.

The term "cDNA library" used herein denotes a library composed of complementary DNAs which are reverse-transcribed from mRNAs.

The term "complement" used herein denotes a polynucleotide sequence capable of forming base pairing with another polynucleotide sequence. For example, the sequence 5'-ATGGACTTACT-3' binds to the complementary sequence 5'-AGTAAGTCCAT-3'.

The term "deletion" used herein denotes a removal of a portion of one or more amino acid residues/nucleotides from a gene.

The term "expressed sequence tags (ESTs)" used herein denotes short (200 to 500 base pairs) nucleotide sequence that derives from either 5' or 3' end of a cDNA.

The term "expression vector" used herein denotes nucleic acid constructs which contain a cloning site for introducing the DNA into vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell" used herein denotes a cell which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition" used herein denotes the addition of a portion of one or more amino acid residues/nucleotides to a gene.

The term "in silico" used herein denotes a process of using computational methods (e.g., BLAST) to analyze DNA sequences.

The term "polymerase chain reaction (PCR)" used herein denotes a method which increases the copy number of a nucleic acid sequence using a DNA polymerase and a set of primers (about 20 bp oligonucleotides complementary to each strand of DNA) under suitable conditions (successive rounds of primer annealing, strand elongation, and dissociation).

The term "protein" or "polypeptide" used herein denotes a sequence of amino acids in a specific order that can be encoded by a gene or by a recombinant DNA. It can also be chemically synthesized.

The term "nucleic acid sequence" or "polynucleotide" used herein denotes a sequence of nucleotide (guanine, cytosine, thymine or adenine) in a specific order that can be a natural or synthesized fragment of DNA or RNA. It may be single-stranded or double-stranded.

The term "reverse transcriptase-polymerase chain reaction (RT-PCR)" used herein denotes a process which transcribes mRNA to complementary DNA strand using reverse transcriptase followed by polymerase chain reaction to amplify the specific fragment of DNA sequences.

The term "transformation" used herein denotes a process describing the uptake, incorporation, and expression of exogenous DNA by prokaryotic host cells.

The term "transfection" used herein a process describing the uptake, incorporation, and expression of exogenous DNA by eukaryotic host cells.

The term "variant" used herein denotes a fragment of sequence (nucleotide or amino acid) inserted or deleted by one or more nucleotides/amino acids.

According to the present invention, the polypeptides of one novel human KIP2-related gene variant and fragments thereof, and the nucleic acid sequences encoding the same are provided.

Figure 1:
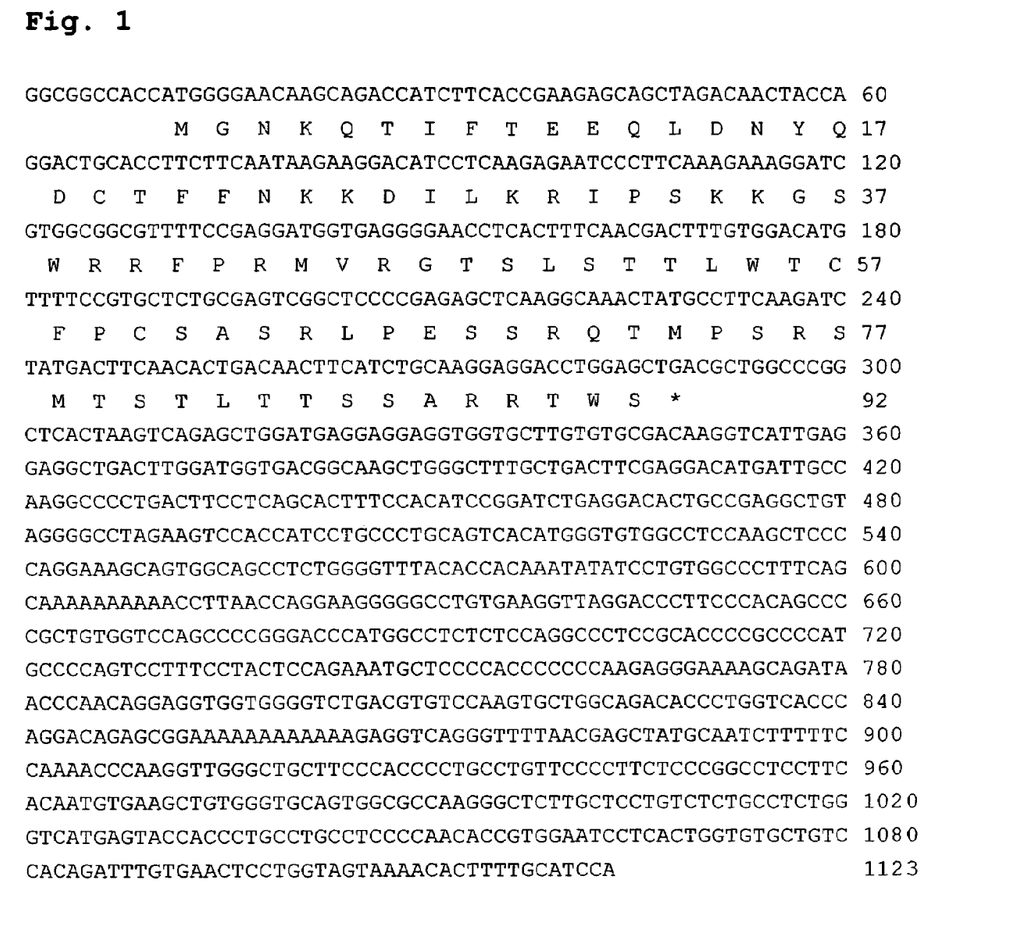
FIG. 1 shows the nucleic acid sequence (SEQ ID NO:1) and amino acid sequence (SEQ ID NO:2) of KIP2V.

According to the present invention, human KIP2 cDNA sequence was used to query the human lung EST databases (a normal lung, a large cell lung cancer, a squamous cell lung cancer and a small cell lung cancer) using BLAST program to search for KIP2-related gene variants. One human cDNA partial sequences (i.e., EST) showing similar to KIP2 was identified. The cDNA clone, named KIP2V (KIP2 variant), was then isolated from lung cancer cDNA library and sequenced. FIG. 1 shows the nucleic acid sequences (SEQ ID NO:1) of KIP2V and its corresponding amino acid sequences (SEQ ID NO:2) encoded thereby.

Figure 2A:
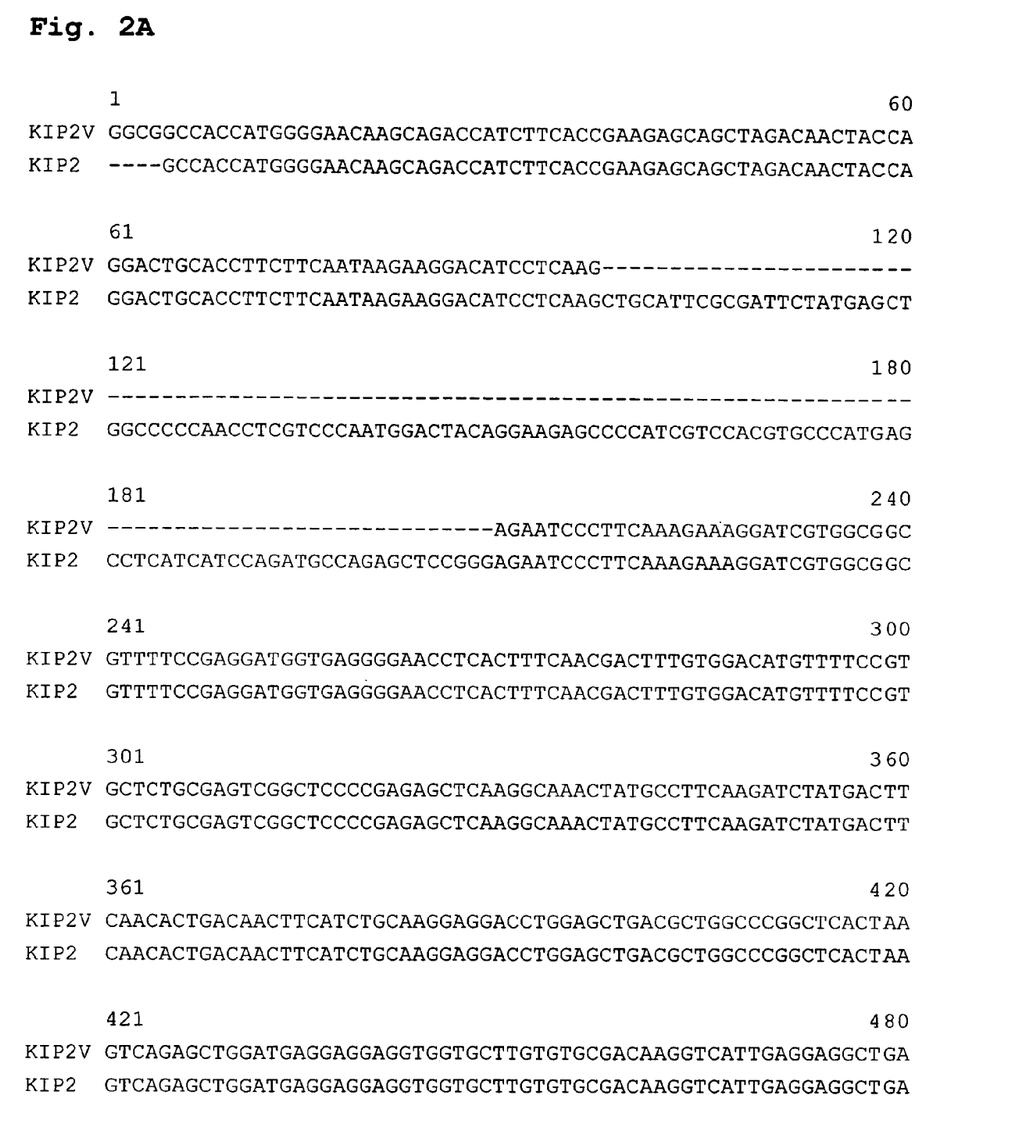
FIGS. 2A, 2B and 2C show the nucleotide sequence alignment between the human KIP2 gene and its related gene variant (KIP2V).
Figure 2B:
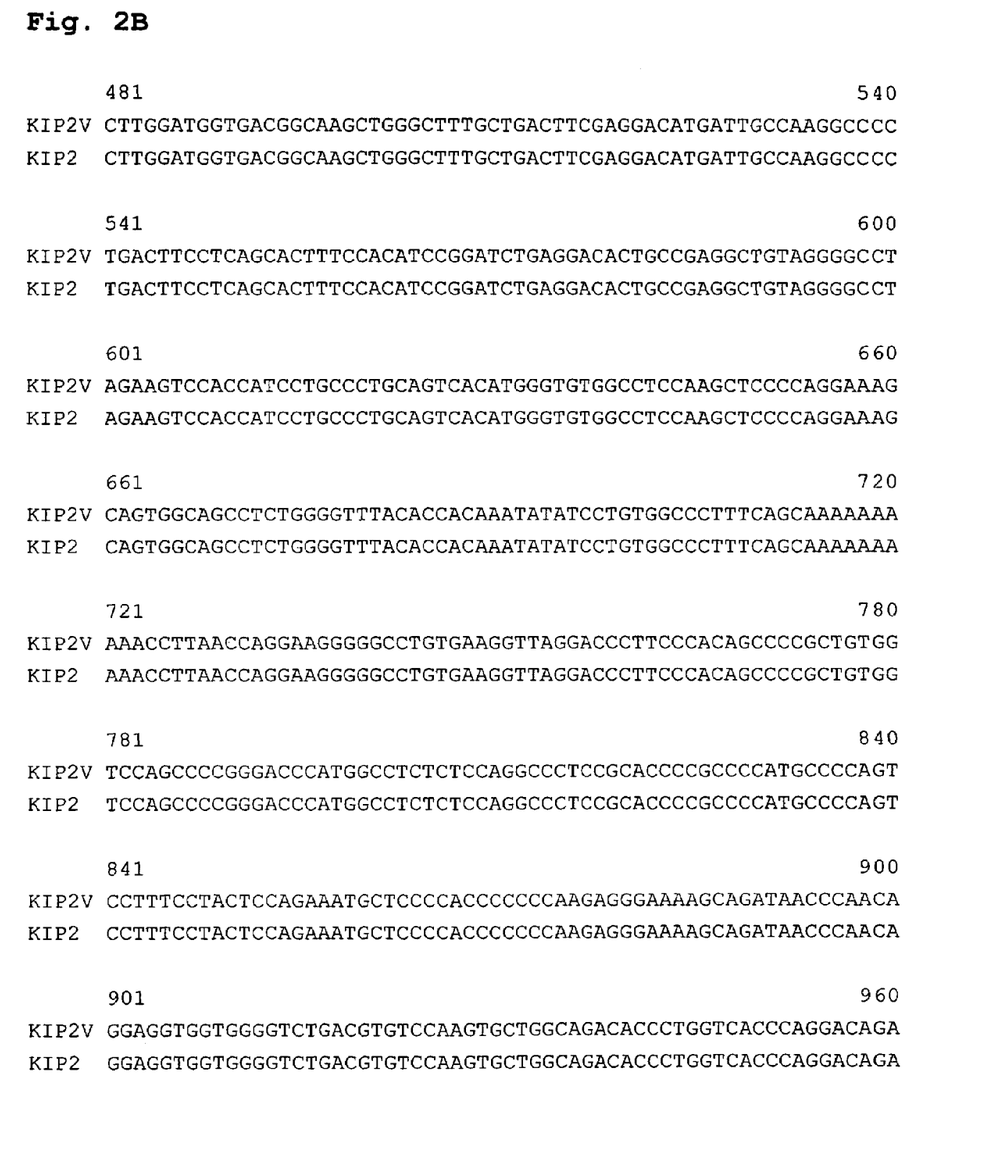
Figure 2C:
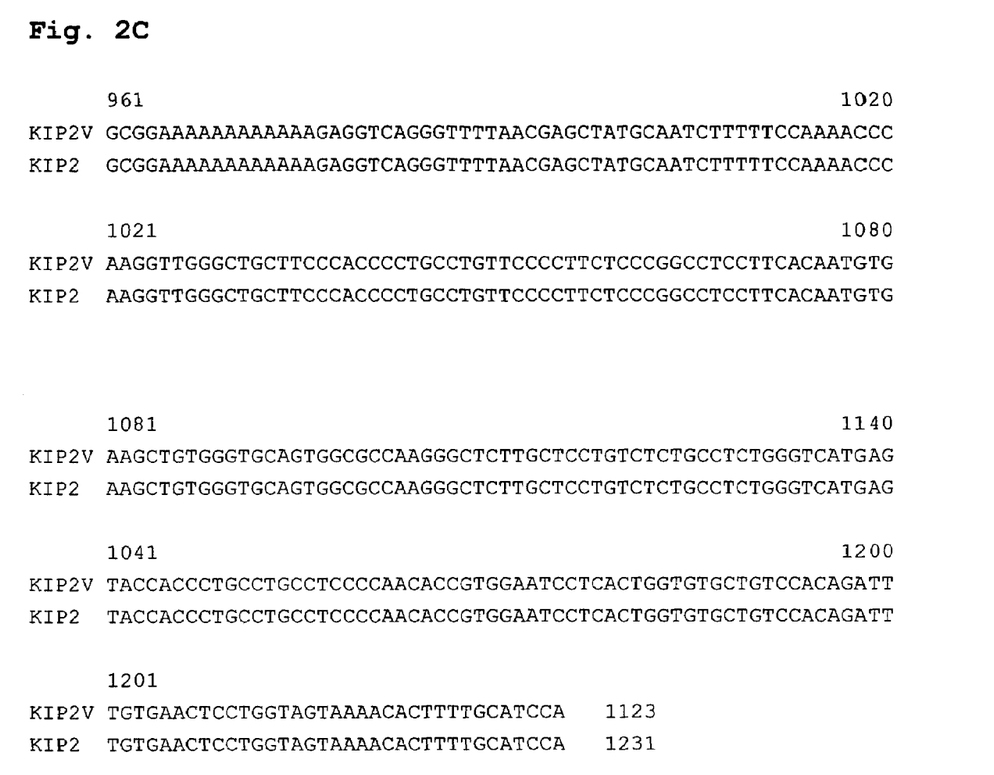
Figure 3:
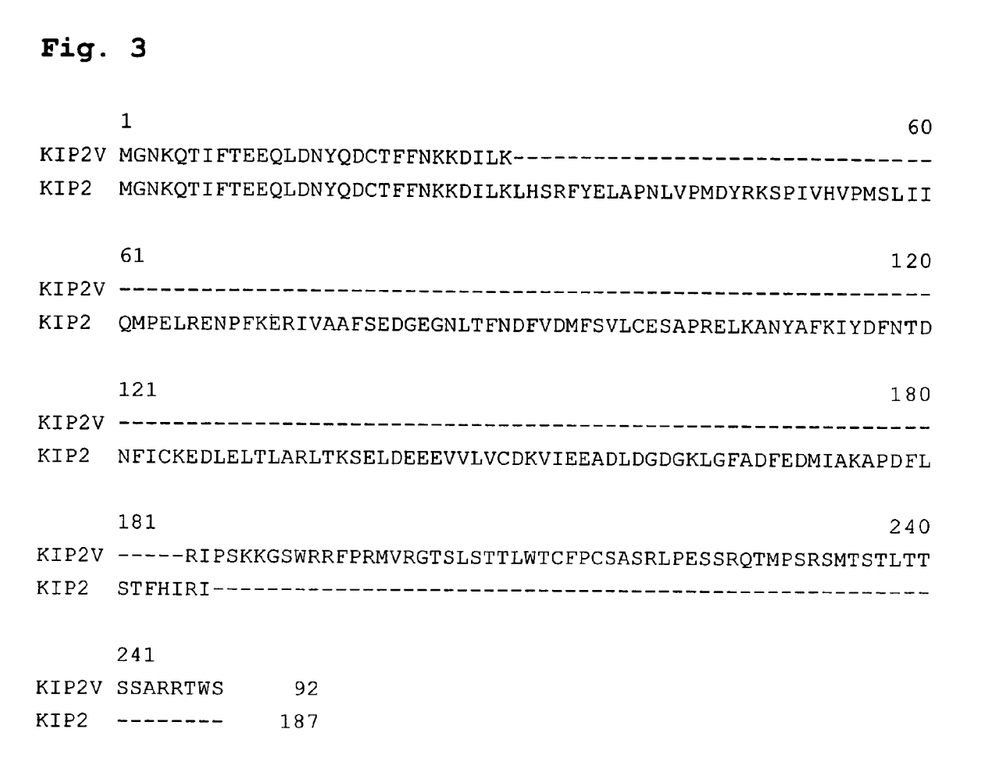
FIG. 3 shows the amino acid sequence alignment between the human KIP2 protein and its related gene variant (KIP2V).

The full-length of the KIP2V cDNA is a 1123 bp clone containing a 276 bp open reading frame (ORF) extending from 11 bp to 286 bp, which corresponds to an encoded protein of 92 amino acid residues with a predicted molecular mass of 10.7 kDa. The sequence around the initiation ATG codon of KIP2V (located at nucleotide 11 to 13 bp) was matched to the Kozak consensus sequence (A/GCCATGG) (Kozak, (1987) Nucleic Acids Res. 15: 8125-48; Kozak, (1991) J Cell Biol. 115: 887-903.). To determine the variation in sequence of KIP2V cDNA clone, an alignment of KIP2 nucleotide/amino acid sequence with KIP2V was performed (FIGS. 2 and 3). The results indicate that one major genetic deletion was found in the aligned sequences showing that KIP2V is a 112 bp deletion in the sequence of KIP2 from 93-209 bp. The lacking of 112 bp generates a frame-shift starting from the amino acid position 30 of KIP2. The predicted amino acid sequence indicated that only the N-terminal section (the first 29 amino acids) of KIP2 is still conserved on KIP2V protein.

In the present invention, a search of ESTs deposited in dbEST (Boguski et al. (1993) Nat Genet. 4: 332-3) at NCBI was performed to determine the tissue distribution of V in silico. The result of in silico Northern analysis showed that one EST (GenBank accession number AI817087) was found to confirm the absence of 112 bp region on KIP2V nucleotide sequence. This EST was generated from a squamous cell lung cancer cDNA library suggesting that the absence of 112 bp nucleotide fragment located between 97-98 bp of KIP2V may serve as a useful marker for diagnosing squamous cell lung cancer. Therefore, any nucleotide fragments comprising 97-98 bp of KIP2V may be used as probes for determining the presence of KIP2V under high stringency conditions. An alternative approach is that any set of primers for amplifying the fragment containing 97-98 bp of KIP2V may be used for determining the presence of the variant.

Scanning the KIP2V sequence against the profile entries in PROSITE (ScanProsite) indicated that KIP2V protein contains four protein kinase C phosphorylation sites (33-35aa, 37-39aa, 68-70aa and 86-88aa), one cAMP- and cGMP-dependent protein kinase phosphorylation site (34-

37aa), two N-myristoylation sites (2-7aa, and 47-52aa), and one Signal peptidases I serine active site (75-82aa).

According to the present invention, the polypeptides of the human KIP2V and its fragments thereof may be produced through genetic engineering techniques. In this case, they are produced by appropriate host cells which have been transformed by DNAs that code for the polypeptides or fragments thereof. The nucleotide sequence encoding the polypeptide of the human KIP2V or their fragments thereof is inserted into an appropriate expression vector, i.e., a vector which contains the necessary elements for the transcription and translation of the inserted coding sequence in a suitable host. The nucleic acid sequence is inserted into the vector in a manner that it will be expressed under appropriate conditions (e.g., in proper orientation and correct reading frame and with appropriate expression sequences, including an RNA polymerase binding sequence and a ribosomal binding sequence).

Any method that is known to those skilled in the art may be used to construct expression vectors containing sequences encoding the polypeptides of the human KIP2-related gene variant (KIP2V) and appropriate transcriptional/translational control elements. These methods may include in vitro recombinant DNA and synthetic techniques, and in vivo genetic recombinants. (See, e.g., Sambrook, J. Cold Spring Harbor Press, Plainview N.Y., ch. 4, 8, and 16-17; Ausubel, R. M. et al. (1995) Current protocols in Molecular Biology, John Wiley & Sons, New York N.Y., ch. 9, 13, and 16.)

A variety of expression vector/host systems may be utilized to express the polypeptide-coding sequence. These include, but not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and most preferably, the bacterium is E. coli.

Alternatively, the Polypeptides of the human KIP2-related gene variant (KIP2V) or fragments thereof may be synthesized using chemical methods. For example, peptide synthesis can be performed using various solid-phase techniques (Roberge, J. Y. et al. (1995) Science 269: 202 to 204). Automated synthesis may be achieved using the ABI 431A peptide synthesizer (Perkin-Elmer).

According to the present invention, the fragments of the polypeptides and nucleic acid sequences of the human KIP2-related gene variant (KIP2V) are used as immunogens and primers or probes, respectively. Preferable, the purified fragments of the human KIP2V are used. The fragments may be produced by enzyme digestion, chemical cleavage of isolated or purified polypeptide or nucleic acid sequences, or chemical synthesis and then may be isolated or purified. Such isolated or purified fragments of the polypeptides and nucleic acid sequences can be used directly as immunogens and primers or probes, respectively.

The present invention further provides the antibodies which specifically bind one or more out-surface epitopes of the polypeptides of the human KIP2V.

According to the present invention, immunization of mammals with immunogens described herin, preferably humans, rabbits, rats, mice, sheep, goats, cows, or horses, is performed following procedures well known to those skilled in the art, for the purpose of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. No. 4,271,145 and U.S. Pat. No. 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using column chromatography methods well known to those skilled in the art.

According to the present invention, antibody fragments which contain specific binding sites for the polypeptides or fragments thereof may also be generated. For example, such fragments include, but are not limited to, $F(ab')_2$ fragments produced by pepsin digestion of the antibody molecule and Fab fragments generated by reducing the disulfide bridges of the $F(ab')_2$ fragments.

The subject invention also provides methods for diagnosing the diseases associated with the gene variant (KIP2V) of the invention, in particular, cancers, more preferably, small cell lung cancer, lung adenocarcinoma, T-cell lymophoblastic lymphoma, glioblastoma, gastric carcinoma, colon adenocarcinoma, prostate carcinoma, pancreatic carcinoma, esophagus epidermoid carcinoma and promonocytic leukemia, by the utilization of the nucleic acid sequences, the polypeptide of the human KIP2-related gene variant (KIP2V), or fragments thereof, and the antibodies against the polypeptides.

Many gene variants have been found to be associated with diseases (Stallings-Mann et al., (1996) Proc Natl Acad Sci USA 93: 12394-9; Liu et al., (1997) Nat Genet 16:328-9; Siffert et al., (1998) Nat Genet 18: 45 to 8; Lukas et al., (2001) Cancer Res 61: 3212 to 9). Since KIP2V clone was isolated from lung cancer cDNA library and together with its higher expression in small cell lung cancer, lung adenocarcinoma, T-cell lymophoblastic lymphoma, glioblastoma, gastric carcinoma, colon adenocarcinoma, prostate carcinoma, pancreatic carcinoma, esophagus epidermoid carcinoma and promonocytic leukemia, it is advisable that KIP2V may serve as markers for the diagnosis of human cancers. Thus, the expression level of KIP2V relative to KIP2 may be a useful indicator for screening of patients suspected of having cancers or more specifically small cell lung cancer, lung adenocarcinoma, T-cell lymophoblastic lymphoma, glioblastoma, gastric carcinoma, colon adenocarcinoma, prostate carcinoma, pancreatic carcinoma, esophagus epidermoid carcinoma and promonocytic leukemia. This suggests that the index of relative expression level (mRNA or protein) may confer an increased susceptibility to cancers, more preferablly, small cell lung cancer, lung adenocarcinoma, T-cell lymophoblastic lymphoma, glioblastoma, gastric carcinoma, colon adenocarcinoma, prostate carcinoma, pancreatic carcinoma, esophagus epidermoid carcinoma and promonocytic leukemia. Fragments of KIP2V transcripts (mRNAs) may be detected by RT-PCR approach. Polypeptides of KIP2V may be determined by the binding of antibodies to these polypeptides. These approaches may be performed in accordance with conventional methods well known to persons skilled in the art.

According to the present invention, the expression of these gene variant mRNAs in sample may be determined by, but not limited to, RT-PCR. Using TRIZOL reagents (Life Technology), total RNA may be isolated from patient samples. Tissue samples (e.g., biopsy samples) are powdered under liquid nitrogen before homogenization. RNA purity and integrity are assessed by absorbance at 260/280 nm and by agarose gel electrophoresis. A set of primers can be designed to amplify the expected size of specific PCR fragments of KIP2V. For example, one of the primers is a fragment complementary to the sequences containing 95-100 bp of KIP2V, and the other is designed complementary to any location of the KIP2V sequence. Alternatively, one primer is complementary to a portion upstream of 97 bp of KIP2V and the other is complementary to a portion downstream of 98 bp of KIP2V, the length of the PCR fragment from KIP2V will be 112 bp shorter than that from KIP2. PCR fragments are analyzed on a 1% agarose gel using five microliters (10%) of the amplified products. The intensity of the signals may be determined by using the Molecular Analyst program (version 1.4.1; Bio-Rad). Thus, the index of relative expression levels for each co-amplified PCR product may be calculated based on the intensity of signals. The primer of the present invention contains 6 to 50 nucleotides, preferably 10 to 40 nucleotides, more preferably 15 to 30 nucleotides.

The RT-PCR experiment may be performed according to the manufacturer instructions (Boehringer Mannheim). A 50 µl reaction mixture containing 2 µl total RNA (0.1 µg/µl), 1 µl each primer (20 pM), 1 µl each dNTP (10 mM), 2.5 µl DTT solution (100 mM), 10 µl 5× RT-PCR buffer, 1 µl enzyme mixture, and 28.5 µl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

The expression of gene variants can also be analyzed using Northern Blot hybridization approach. Specific fragment comprising 95 to 100 of the KIP2V may be amplified by polymerase chain reaction (PCR) using primer set designed for RT-PCR. The amplified PCR fragment may be labeled and may serve as a probe to hybridize the membranes containing total RNAs extracted from the samples under the conditions of 55° C. in a suitable hybridization solution for 3 hr. Blots may be washed twice in 2×SSC, 0.1% SDS at room temperature for 15 minutes each, followed by two washes in 0.1×SSC and 0.1% SDS at 65° C. for 20 minutes each. After these washes, blots may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of gene variants (cDNAs or PCR) can be detected using microarray approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the invention, the method for diagnosing the diseases associated with the deficiency of human KIP2 gene may also be performed by detecting the polypeptide encoded by the KIP2V of the invention. For instance, the polypeptide in protein samples obtained from the mammal may be determined by, but not limited to, the immunoassay wherein the antibodies specifically binding to the polypeptides of the invention is contacted with the sample, and the antibody-polypeptide binding complex is detected. If necessary, the amount of antibody-polypeptide binding complex can be determined.

The polypeptides of the gene variants may be expressed in prokaryotic cells by using suitable prokaryotic expression vectors. The cDNA fragments of KIP2V gene encoding the amino acid coding sequence may be PCR amplified using primer set with restriction enzyme digestion sites incorporated in the 5' and 3' ends, respectively. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., *E. coli* BL21 (DE3)). Recombinant protein synthesis may be stimulated by the addition of 0.4 mM isopropylthiogalactoside (IPTG) for 3 h. The bacterially-expressed proteins may be purified.

the polypeptide of the gene variant may be expressed in animal cells by using eukaryotic expression vectors. Cells may be maintained in Dulbecco's modified Eagle's medium (DMEM) supplemented with 10% fetal bovine serum (FBS; Gibco BRL) at 37° C. in a humidified 5% $CO_2$ atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of $5 \times 10^4$ cells per well. Transfections may be carried out using Lipofectaminutese Plus transfection reagent according to the manufacturer's instructions (Gibco BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins. After these proteins are purified, monoclonal antibodies against these purified proteins (KIP2V) may be generated using hybridoma technique according to the conventional methods (de StGroth and Scheidegger, (1980) J Immunol Methods 35:1-21; Cote et al. (1983) Proc Natl Acad Sci USA 80: 2026-30; and Kozbor et al. (1985) J Immunol Methods 81:31-42).

According to the present invention, the presence of the polypeptides of the gene variant in samples of cancers may be determined by, but not limited to, Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 h at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody directed against the polypeptides of gene variants. Unbound antibody is removed by washing with TBST for 5×1 minutes. Bound antibody may be detected using commercial ECL Western blotting detecting reagents.

The following examples are provided for illustration, but not for limiting the invention.

EXAMPLES

Analysis of Human Lung EST Databases

Expressed sequence tags (ESTs) generated from the large-scale PCR-based sequencing of the 5'-end of human lung (normal, SCLC, squamous cell lung cancer and large cell lung cancer) cDNA clones were compiled and served as EST databases. Sequence comparisons against the nonredundant nucleotide and protein databases were performed using BLASTN and BLASTX programs (Altschul et al., (1997) Nucleic Acids Res. 25: 3389-3402; Gish and States, (1993) Nat Genet 3:266-272), at the National Center for Biotechnology Information (NCBI) with a significance cutoff of $p<10^{-10}$. ESTs representing putative KIP2V gene were identified during the course of EST generation.

Isolation of cDNA Clones

One cDNA clone exhibiting EST sequence similar to the KIP2 gene was isolated from the lung cancer cDNA library and named KIP2V. The inserts of these clones were subsequently excised in vivo from the λZAP Express vector using the ExAssist/XLOLR helper phage system (Stratagene). Phagemid particles were excised by coinfecting XL1-BLUE MRF' cells with ExAssist helper phage. The excised pBluescript phagemids were used to infect E. coli XLOLR cells, which lack the amber suppressor necessary for ExAssist phage replication. Infected XLOLR cells were selected using kanamycin resistance. Resultant colonies contained the double stranded phagemid vector with the cloned cDNA insert. A single colony was grown overnight in LB-kanamycin, and DNA was purified using a Qiagen plasmid purification kit.

Full Length Nucleotide Sequencing and Database Comparisons

Phagemid DNA was sequenced using the Epicentre#SE9101LC SequiTherm EXCEL™ II DNA Sequencing Kit for 4200S-2 Global NEW IR² DNA sequencing system (LI-COR). Using the primer-walking approach, full-length sequence was determined. Nucleotide and protein searches were performed using BLAST against the non-redundant database of NCBI.

In Silico Tissue Distribution (Northern) Analysis

The coding sequence for each cDNA clones was searched against the dbEST sequence database (Boguski et al., (1993) Nat Genet. 4: 332-3) using the BLAST algorithm at the NCBI website. ESTs derived from each tissue were used as a source of information for transcript tissue expression analysis. Tissue distribution for each isolated cDNA clone was determined by ESTs matching to that particular sequence variants (insertions or deletions) with a significance cutoff of $p<10^{-10}$.

RT-PCR expression Analysis

Figure 4A:
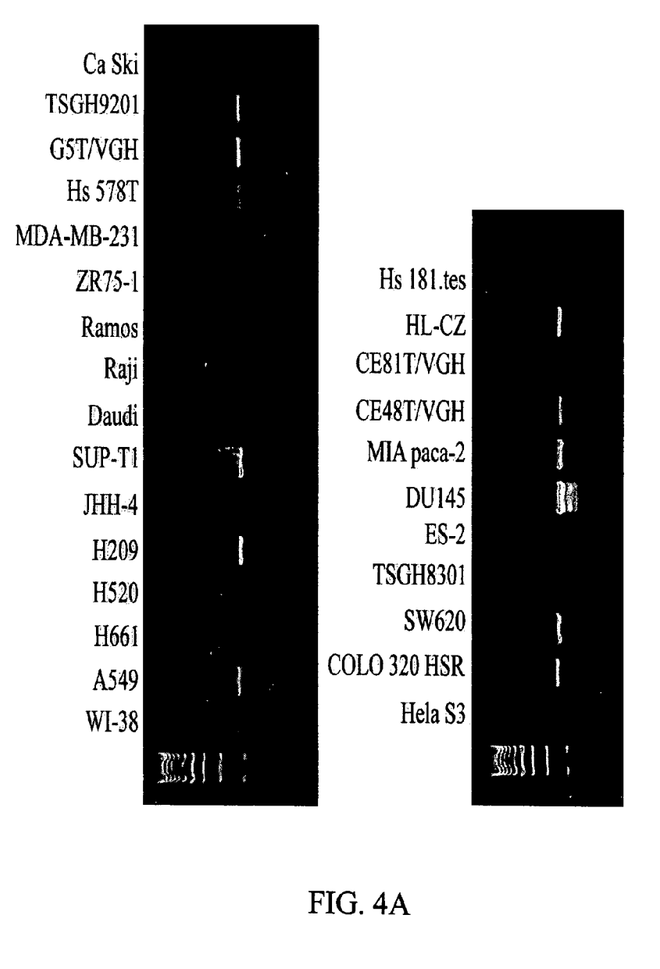
FIGS. 4A and 4B show the RT-PCR analysis of KIP2V and GAPDH (internal control) expressions, respectively, in 27 cell lines.
Figure 4B:
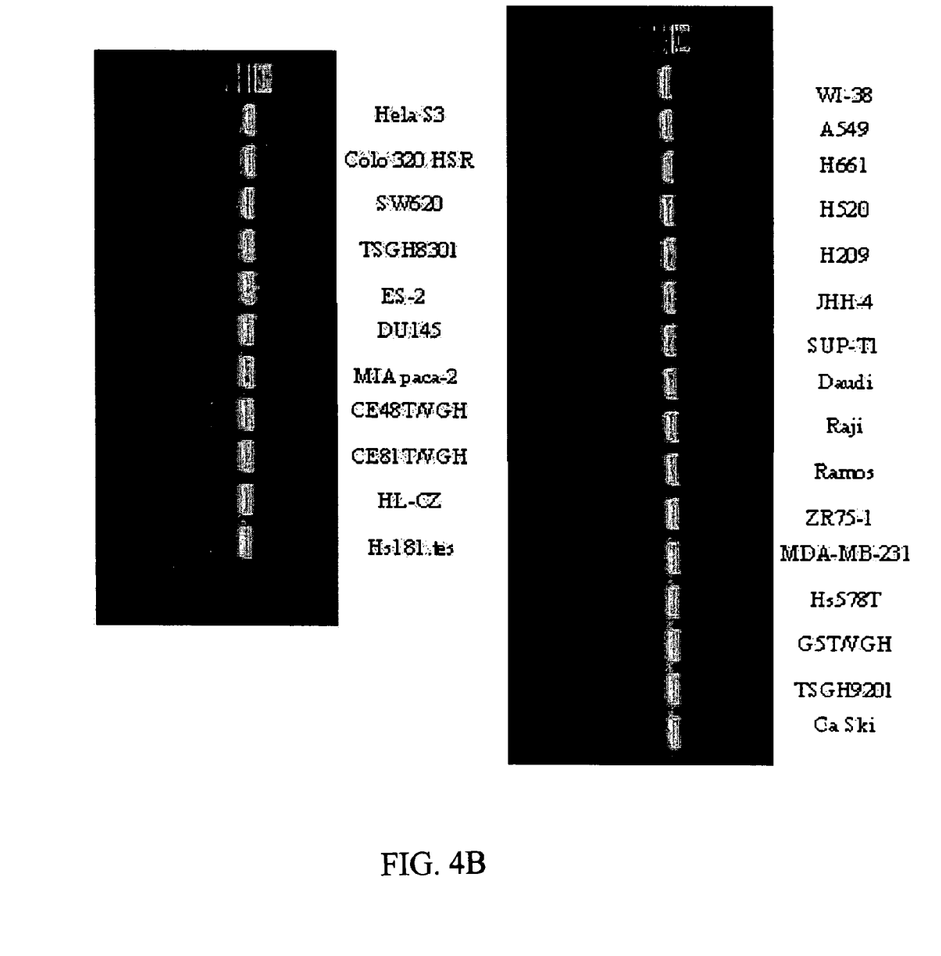

RT-PCR analysis of KIP2V was conducted in 27 human cell lines (WI38: lung, fetus; A549: lung adenocarcinoma; H661: large cell carcinoma, lung; H520: squamous cell carcinoma, lung; H209: small cell carcinoma, lung; JHH-4: hepatoma; SUP-T1: T-cell lymophoblastic lymphoma; Daudi: Burkitt,s lymophoma; RAJI: Burkitt,s lymophoma; Ramo: Burkitt,s lymophoma; ZR75-1: breast carcinoma; MDA-MB-231: breast adenocarcinoma; Hs 578T: breast carcinoma; G5T/VGH: glioblastoma multiforme; TSGH9201: gastric carcinoma; Ca Ski: cervix epidermoid carcinoma; Hela S3: cervical epitheloid carcinoma; COLO 320 HSR: colon adenocarcinoma; SW620: adenocarcinoma; TSGH8301: urinary bladder carcinoma; ES-2: ovarian carcinoma; DU145: brain prostate carcinoma; MIA paca-2: pancreatic carcinoma; CE48T/VGH: esophagus epidermoid carcinoma; CE81T/VGH: esophagus carcinoma well differentiated aquamous; HL-CZ: promonocytic leukemia; Hs 181.tes: normal testis). A pair of primers (forward: ACATC-CTCAAGAGAATCCCTTC (SEQ ID NO:5); reverse: GCT-CACTAAGTCAGAGCTGGAT (SEQ ID NO:6) was designed for the RT-PCR analysis. The products of RT-PCR, electrophoresed in 1% agarose gel, show the presence of KIP2V mRNA with the expected sizes of approximately 235 bp (FIG. 4A). RT-PCR analysis of Glyceraldehyde phosphate dehydrogenase (GAPDH) was used as an internal control (FIG. 4B). Shown on the left side of FIGS. 4A and B are 100 bp DNA ladder markers. It should be noted that KIP2V mRNA was highly expressed in the cell line of the small cell lung cancer, lung adenocarcinoma, T-cell lymophoblastic lymphoma, glioblastoma, gastric carcinoma, colon adenocarcinoma, prostate carcinoma, pancreatic carcinoma, esophagus epidermoid carcinoma and promonocytic leukemiaprostate carcinoma suggesting that KIP2V may be used for diagnosing cancers.

REFERENCES

Adkins and Lumb, Intrinsic structural disorder and sequence features of the cell cycle inhibitor p57(Kip2). Proteins, 46:1-7 (2002).

Altschul et al., Gapped BLAST and PSI-BLAST: a new generation of protein database search programs, Nucleic Acids Res, 25: 3389-3402, (1997).

American Cancer Society (ACS), Atlanta, Ga. Cancer Facts & Figures-2005, 2005

Ausubel et al., Current protocols in Molecular Biology, John Wiley & Sons, New York N.Y., ch. 9, 13, and 16, (1995).

Boguski et al., dbEST—database for "expressed sequence tags". Nat Genet. 4: 332-3, (1993).

Chung et al. Chromosome 11p15.5 regional imprinting: comparative analysis of KIP2 and H19 in human tissues and Wilms' tumors. Hum Mol Genet 5:1101-8 (1996).

Cote et al., Generation of human monoclonal antibodies reactive with cellular antigens, Proc Natl Acad Sci USA 80: 2026-30 (1983).

Dauphinot et al. Analysis of the expression of cell cycle regulators in Ewing cell lines: EWS-FLI-1 modulates p57KIP2and c-Myc expression. Oncogene 20:3258-65, (2001)

de StGroth and Scheidegger, Production of monoclonal antibodies: strategy and tactics, J Immunol Methods 35:1-21, (1980).

Gish and States, Identification of protein coding regions by database similarity search, Nat Genet, 3:266-272, (1993).

Harper and Elledge, Cdk inhibitors in development and cancer. Curr Opin Genet Dev 6:56-64, (1996).

Ito et al. Expression of p57/Kip2 protein in hepatocellular carcinoma. Oncology, 61:221-5, (2001)

Kozak, An analysis of 5'-noncoding sequences from 699 vertebrate messenger RNAs. Nucleic Acids Res, 15: 8125-48, (1987).

Kozak, An analysis of vertebrate mRNA sequences: intimations of translational control, J Cell Biol, 115: 887-903, (1991).

Kozbor et al., Specific immunoglobulin production and enhanced tumorigenicity following ascites growth of human hybridomas, J Immunol Methods, 81:31-42 (1985).

Lee and Yang, Negative regulators of cyclin-dependent kinases and their roles in cancers. Cell Mol Life Sci 58:1907-22, (2001).

Lee et al. Cloning of p57KIP2, a cyclin-dependent kinase inhibitor with unique domain structure and tissue distribution. Genes Dev 9:639-49, (1995).

Liu et al., Silent mutation induces exon skipping of fibrillin-1gene in Marfan syndrome. Nat Genet 16:328-9, (1997).

Lukas et al., Alternative and aberrant messenger RNA splicing of the mdm2 oncogene in invasive breast cancer. Cancer Res 61:3212-9, (2001).

Matsuoka et al. p57KIP2, a structurally distinct member of the p21CIP1 Cdk inhibitor family, is a candidate tumor suppressor gene. Genes Dev 9:650-62, (1995).

Oya and Schulz, Decreased expression of p57(KIP2) mRNA in human bladder cancer. Br J Cancer 83:626-31, (2000).

Roberge et al., A strategy for a convergent synthesis of N-linked glycopeptides on a solid support. Science 269:202-4, (1995).

Sambrook, J. Cold Spring Harbor Press, Plainview N.Y., ch. 4, 8, and 16-17.

Sherr, Cancer cell cycles. Science 274:1672-7, (1996).

Siffert et al., Association of a human G-protein beta3 subunit variant with hypertension. Nat Genet, 18:45-8, (1998).

Stallings-Mann et al., Alternative splicing of exon 3 of the human growth hormone receptor is the result of an unusual genetic polymorphism. Proc Natl Acad Sci USA 93:12394-9, (1996).

Strausberg, R. EST Accession No. AI817087

Watanabe et al. Suppression of cell transformation by the cyclin-dependent kinase inhibitor p57KIP2 requires binding to proliferating cell nuclear antigen. Proc Natl Acad Sci USA, 95:1392-1397, (1998).

World Health Organization Geneva. National cancer control programmes: policies and managerial guidelines, 2002

What is claimed is:

1. An isolated nucleic acid, which comprises the nucleotide sequence of SEQ ID NO: 1 and encodes an isolated polypeptide comprising the amino acid sequence of SEQ ID NO: 2.

2. An expression vector comprising the nucleic acid of claim 1.

3. An isolated host cell comprising the expression vector of claim 2.

4. A method for producing an isolated polypeptide comprising the amino acid sequence of SEQ ID NO: 2, which comprises the steps of:

(1) culturing the host cell of claim 3 under a condition suitable for the expression of the polypeptide; and (2) recovering the polypeptide from the host cell culture.

* * * * *

```
                        SEQUENCE LISTING

<160> NUMBER OF SEQ ID NOS: 6

<210> SEQ ID NO 1
<211> LENGTH: 1123
<212> TYPE: DNA
<213> ORGANISM: Homo sapiens

<400> SEQUENCE: 1
ggcggccacc atggggaaca agcagaccat cttcaccgaa gagcagctag acaactacca      60
ggactgcacc ttcttcaata agaaggacat cctcaagaga atcccttcaa agaaaggatc     120
gtggcggcgt tttccgagga tggtgagggg aacctcactt tcaacgactt tgtggacatg     180
ttttccgtgc tctgcgagtc ggctccccga gagctcaagg caaactatgc cttcaagatc     240
tatgacttca cactgacaa cttcatctgc aaggaggacc tggagctgac gctggcccgg     300
ctcactaagt cagagctgga tgaggaggag gtggtgcttg tgtgcgacaa ggtcattgag     360
gaggctgact tggatggtga cggcaagctg ggctttgctg acttcgagga catgattgcc     420 aaggccctg acttcctcag cactttccac atccggatct gaggacactg ccgaggctgt     480 agggggcctag aagtccacca tcctgccctg cagtcacatg ggtgtggcct ccaagctccc     540
caggaaagca gtggcagcct ctggggttta caccacaaat atatcctgtg gcccctttcag     600 caaaaaaaaa accttaacca ggaaggggggc ctgtgaaggt taggacccctt cccacagccc     660 cgctgtggtc cagccccggg acccatggcc tctctccagg ccctccgcac cccgccccat     720
gccccagtcc tttcctactc cagaaatgct ccccaccccc caagaggga aaagcagata     780 acccaacagg aggtggtggg gtctgacgtg tccaagtgct ggcagacacc ctggtcaccc     840
aggacagagc ggaaaaaaaa aaaagaggtc agggttttaa cgagctatgc aatcttttc      900 caaacccaa ggttgggctg cttcccaccc ctgcctgttc cccttctccc ggcctccttc       960
```

-continued

```
acaatgtgaa gctgtgggtg cagtggcgcc aagggctctt gctcctgtct ctgcctctgg      1020
gtcatgagta ccaccctgcc tgcctcccca acaccgtgga atcctcactg gtgtgctgtc      1080
cacagatttg tgaactcctg gtagtaaaac acttttgcat cca                        1123
```

```
<210> SEQ ID NO 2
<211> LENGTH: 92
<212> TYPE: PRT
<213> ORGANISM: Homo sapiens

<400> SEQUENCE: 2
```

Met Gly Asn Lys Gln Thr Ile Phe Thr Glu Glu Gln Leu Asp Asn Tyr
1               5                   10                  15

Gln Asp Cys Thr Phe Phe Asn Lys Lys Asp Ile Leu Lys Arg Ile Pro
            20                  25                  30

Ser Lys Lys Gly Ser Trp Arg Arg Phe Pro Arg Met Val Arg Gly Thr
        35                  40                  45

Ser Leu Ser Thr Thr Leu Trp Thr Cys Phe Pro Cys Ser Ala Ser Arg
    50                  55                  60

Leu Pro Glu Ser Ser Arg Gln Thr Met Pro Ser Arg Ser Met Thr Ser
65                  70                  75                  80

Thr Leu Thr Thr Ser Ser Ala Arg Arg Thr Trp Ser
                85                  90

```
<210> SEQ ID NO 3
<211> LENGTH: 11
<212> TYPE: DNA
<213> ORGANISM: Artificial sequence
<220> FEATURE:
<221> NAME/KEY:
<222> LOCATION:
<223> OTHER INFORMATION: A polynucleotide sequence provided to
      illustrate what is meant by the term    "complement"

<400> SEQUENCE: 3
atggacttac t                                                            11

<210> SEQ ID NO 4
<211> LENGTH: 11
<212> TYPE: DNA
<213> ORGANISM: Artificial sequence
<220> FEATURE:
<221> NAME/KEY:
<222> LOCATION:
<223> OTHER INFORMATION: A polynucleotide sequence provided to
      illustrate what is meant by the term    "complement"

<400> SEQUENCE: 4
agtaagtcca t                                                            11

<210> SEQ ID NO 5
<211> LENGTH: 22
<212> TYPE: DNA
<213> ORGANISM: Homo sapiens
<220> FEATURE:
<221> NAME/KEY:
<222> LOCATION:
<223> OTHER INFORMATION: Primer

<400> SEQUENCE: 5
acatcctcaa gagaatccct tc                                                22

<210> SEQ ID NO 6
<211> LENGTH: 22
```

```
-continued

<212> TYPE: DNA
<213> ORGANISM: Homo sapiens
<220> FEATURE:
<221> NAME/KEY:
<222> LOCATION:
<223> OTHER INFORMATION: Primer

<400> SEQUENCE: 6
gctcactaag tcagagctgg at                                              22
```